(12) United States Patent
Burst et al.

(10) Patent No.: US 6,274,744 B1
(45) Date of Patent: Aug. 14, 2001

(54) PREPARATION OF ALKALI METAL SALTS OF L-ASCORBIC ACID

(75) Inventors: Wolfram Burst, Mannheim; Gerd Kaibel, Lampertheim; Andreas Böttcher, Nussloch; Veronique Kessler, Ludwigshafen; Thomas Kuntze, Böhl-Iggelheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/688,882

(22) Filed: Oct. 17, 2000

(30) Foreign Application Priority Data

Nov. 12, 1999 (DE) ............................................... 199 54 511

(51) Int. Cl.$^7$ ................................................. C07D 307/62
(52) U.S. Cl. ............................................................. 549/315
(58) Field of Search .............................................. 549/315

(56) References Cited

U.S. PATENT DOCUMENTS

| | | | |
|---|---|---|---|
| 2,185,383 | 1/1940 | Pasternack et al. | 260/344 |
| 4,491,668 | 1/1985 | Ikawa et al. | 549/315 |
| 5,391,770 | 2/1995 | LeFur et al. | 549/315 |
| 5,744,618 | 4/1998 | Fechtel et al. | 549/315 |
| 5,744,634 | 4/1998 | Veits | 560/174 |

FOREIGN PATENT DOCUMENTS

| | | |
|---|---|---|
| 1 242 309 | 9/1988 | (CA) . |
| 195 47 073 | 11/1996 | (DE) . |
| 126 288 | 11/1984 | (EP) . |
| 133 493 | 2/1985 | (EP) . |
| 403 351 | 12/1990 | (EP) . |
| 671 405 | 9/1995 | (EP) . |
| 1 222 322 | 2/1971 | (GB) . |
| 7315931 | 5/1973 | (JP) . |
| 7 5022113 | 7/1975 | (JP) . |
| 58-177986 | 10/1983 | (JP) . |
| WO 87/00839 | 2/1987 | (WO) . |
| WO 90/08127 | 7/1990 | (WO) . |
| WO 99/07691 | 2/1999 | (WO) . |

OTHER PUBLICATIONS

Lestak et al. "Advanced Distillation Saves Money and Capital", Chemical Engineering (1997) pp. 72–76.

Knott "Distillation's great leap forward?", Process Engineering, (1993) pp. 33–34.

Kaibel "Distillation Columns with Vertical Partitions", Chem. Eng. Technol., vol. 10 (1987) pp. 92–98.

Marcias Machin et al. "Calulate ΔP of a Fixed–Bed Filter", Chemical Engineering, vol. 10 (1998) pp. 159–162.

Ullmann's Encyclopedia of Industrial Chemistry, vol. A27, (1996) pp. 551–557.

Crawford et al. "Systhesis of L–Ascorbic Acid", Advances in Carbohydrate Chemistry and Biochemistry, vol. 37 (1980) pp. 79–155.

Ullmann's Encyklopädie der technischen Chemie 4. Ed. 2 (1972) pp. 516–519.

Ullmann's Encyklopädie der technischen Chemie 4. Ed. Chapter 2 (1972) pp. 533–537.

Ullmann's Encyklopädie der technischen Chemie 4. Ed. Chapter 2 (1972) pp. 533–541.

Ullmann's Encyklopädie der technischen Chemie 4. Ed. Chapter 2 (1972) pp. 652–661.

Ullmann's Encyklopädie der technischen Chemie 4. Ed. Chapter 3 (1973) pp. 386–388, Hartig et al. "Verfahrenstechnische Auslengung einer Veresterungskolonne", Chemie Ingenierur Technik vol. 43, (1971) pp. 1001–1007.

Kaibel et al. "Reaktionen In Sedtillationskolonnen", Chem. Ing. Tech vol. 50 (1978) pp. 586–592.

Popelier "Contribution à Pétude des sulfate acides d'alkyle", Bulletin de la Société Chimiaque de Belquique, vol. 35 (1926) pp. 265–227.

*Primary Examiner*—Amelia Owens
(74) *Attorney, Agent, or Firm*—Keil & Weinkauf

(57) ABSTRACT

A process for preparing alkali metal salts of L-ascorbic acid comprising the following steps:

Figure 1:
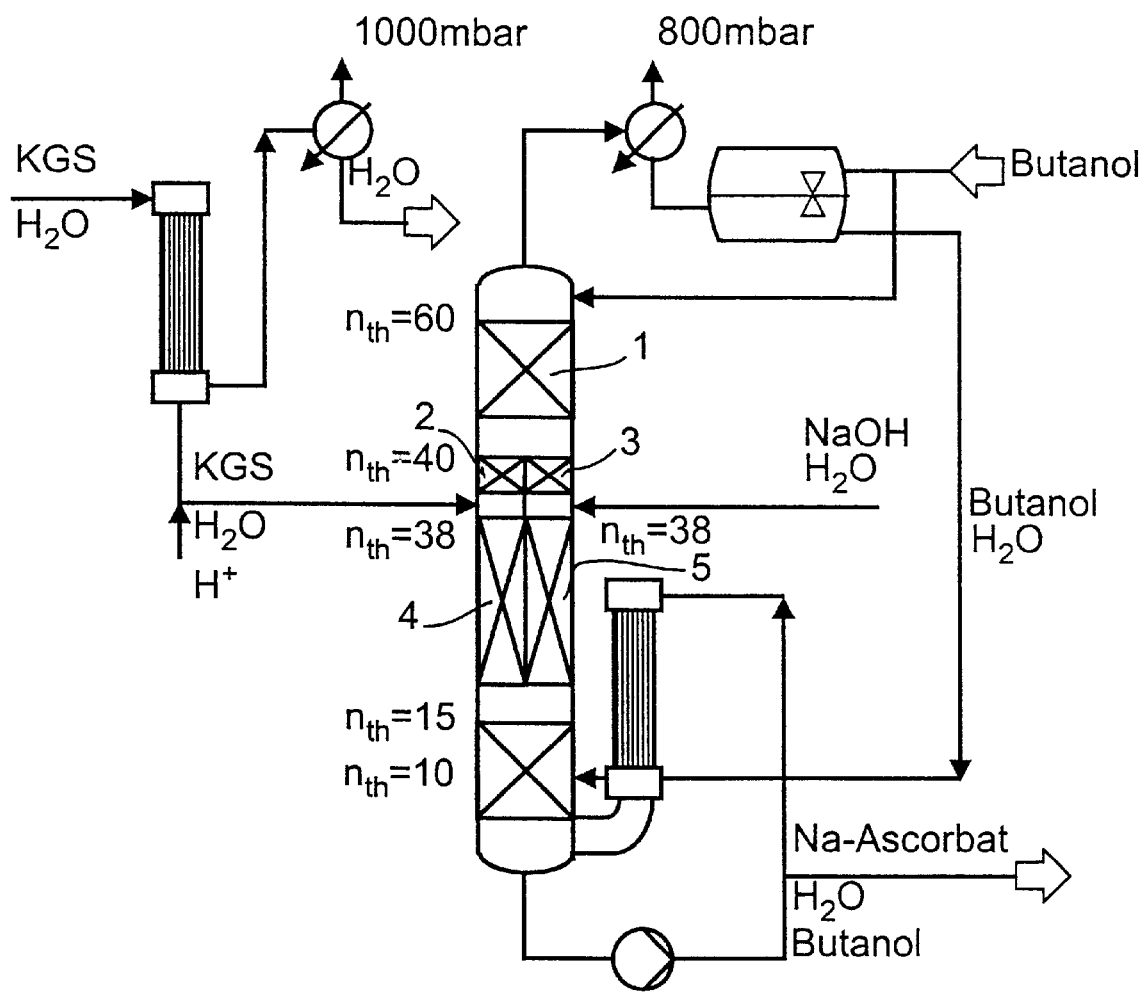

a) esterifying 2-keto-L-gulonic acid or diacetone-2-keto-L-gulonic acid with a $C_1$–$C_{10}$-alkohol in the presence of an acid catalyst, b) rearranging the resultant 2-keto-L-gulonic acid $C_1$–$C_{10}$-alkyl ester in the presence of an alkali metal $C_1$–$C_{10}$-alkoxide, comprises carrying out each of the process steps a) and b) continuously.

17 Claims, 2 Drawing Sheets

PREPARATION OF ALKALI METAL SALTS OF L-ASCORBIC ACID

The present invention relates to a continuous process for preparing alkali metal salts of L-ascorbic acid by esterifying 2-keto-L-gulonic acid or diacetone-2-keto-L-gulonic acid with a $C_1$–$C_{10}$-alcohol in the presence of an acid catalyst and rearranging the resultant 2-keto-L-gulonic acid $C_1$–$C_{10}$-alkyl ester in the presence of an alkali metal $C_1$–$C_{10}$-alkoxide.

For the preparation of L-ascorbic acid, a multiplicity of process variants have been described in the past. An overview may be found, inter alia, in Crawford et al., Adv. Carbohydrate Chem. 37 (1980) 79 and in Ullmann's Encyclopedia of Industrial Chemistry, Vol. A27 (1996) 551–557.

In principle, two process variants have established themselves for the large-scale synthesis of vitamin C—one acid- and one base-catalyzed rearrangement of 2-keto-L-gulonic acid to form L-ascorbic acid or L-ascorbates.

Although the acid-catalyzed lactonization of 2-keto-L-gulonic acid is a simple batch process, it is associated with a high equipment requirement for catalyst removal and isolation of the product of value. The base-catalyzed lactonization is also a classical multistage process which includes the preparation of an ester of 2-keto-L-gulonic acid, the lactonization to the ascorbic acid salt and liberation of the ascorbic acid under acid conditions.

For both synthesis routes, a multiplicity of patents or patent applications are known.

Thus, U.S. Pat. No. 2,185,383 describes reacting 2-keto-L-gulonic acid with concentrated hydrochloric acid and acetic acid as solvent.

Japanese laid-open application 58-177986 describes a process which includes the addition of ethanol and acetone to the sodium salt of 2-keto-L-gulonic acid, neutralization with hydrochloric acid, separating off the sodium chloride which is precipitated out by filtration and then holding the reaction mixture at temperatures in the range from 25° C. to 75° C., as a result of which L-ascorbic acid is obtained.

Japanese published application 48-15931 describes reacting 2-keto-L-gulonic acid with a mineral acid in an inert solvent in the presence of a surface-active substance.

WO 87/00839 claims a process in which a slurry of 2-keto-L-gulonic acid is reacted in an inert organic solvent in the presence of a surface-active compound under acid catalysis to give L-ascorbic acid.

DE-A-195 47 073 describes a process for preparing L-ascorbic acid by reacting 2-keto-L-gulonic acid with aqueous mineral acid in a solvent mixture containing an inert organic solvent, an aliphatic ketone and an acid chloride.

WO 99/07691 describes reacting 2-keto-L-gulonic acid with concentrated hydrochloric acid at from 40 to 80° C.

EP-A-0 671 405 discloses a process for preparing 2-keto-L-gulonic acid methyl ester or ethyl ester by esterifying 2-keto-L-gulonic acid with methanol or ethanol in the presence of an acidic ion exchanger. In addition, it may be read in this application that the abovementioned esters can be subjected to an alkaline rearrangement (lactonization) to give ascorbic acid or a salt thereof.

U.S. Pat. No. 5,391,770 describes esterifying 2-keto-L-gulonic acid, with subsequent base-catalyzed lactonization of the resultant ester to give salts of L-ascorbic acid and liberation of ascorbic acid by addition of a strong acid.

Japanese published application 22 113/75 describes esterifying 2-keto-L-gulonic acid with butanol and the subsequent acid-catalyzed lactonization in benzene as solvent.

The acid-catalyzed lactonization generally requires long reaction times and therefore large apparatus volumes, the use of an inert solvent and a complex catalyst separation.

More favorable space-time yields are achieved in the base-catalyzed lactonization by more rapid rearrangement of the ester. However, with this synthesis route, complete esterification of the 2-keto-L-gulonic acid must be ensured and anhydrous reaction conditions maintained to avoid saponification reactions. This is not always achieved satisfactorily in general, despite the use of a stirred-tank cascade and complex dehydration of the esterification alcohol.

The base-catalyzed lactonization, for example with $NaHCO_3$ or NaOH in methanol, generally gives unreacted 2-keto-L-gulonic acid as an unwanted byproduct in the sodium ascorbate. In addition, when, for example, sodium hydroxide solution is used in methanol, the high water content leads to unwanted discolored byproducts and to a reduction in yield owing to the high solubility of sodium ascorbate in water.

To date, only continuous processes for esterifying 2-keto-L-gulonic acid have been described (see EP-A-0 671 405). In contrast, lactonization according to the prior art to date is a classical batch process.

It is an object of the present invention, therefore, to provide a process for preparing alkali metal salts of L-ascorbic acid which does not have the abovementioned disadvantages.

We have found that this object is achieved by a process for preparing alkali metal salts of L-ascorbic acid comprising the following steps:

a) esterifying 2-keto-L-gulonic acid or diacetone-2-keto-L-gulonic acid with a $C_1$–$C_{10}$-alcohol in the presence of an acid catalyst, b) rearranging the 2-keto-L-gulonic acid $C_1$–$C_{10}$-alkyl ester formed in the presence of an alkali metal $C_1$–$C_{10}$-alkoxide, which comprises carrying out each of the process steps a) and b) continuously.

Alkali metal salts of L-ascorbic acid preferably meant are sodium, potassium and lithium salts, particularly preferably sodium salts.

Suitable $C_1$–$C_{10}$-alcohols for esterifying 2-keto-L-gulonic acid or diacetone-2-keto-L-gulonic acid in process step a) are in principle all $C_1$–$C_{10}$-alcohols, advantageously saturated, branched or unbranched alkyl alcohols having a carbon number greater than or equal to 3, preferably alcohols having an alkyl residue of from 3 to 10 carbons, for example n-propanol, isopropanol, 1-butanol, 2-butanol, 2-methyl-1-propanol, 2-methyl-2-propanol, 1-pentanol, 2-pentanol, 3-pentanol, 1-hexanol, 2-hexanol, 1-heptanol, 2-heptanol, 1-octanol, 2-octanol, 3-octanol, 1-nonanol, 2-nonanol, 1-decanol, 2-decanol, 4-decanol, particularly preferably $C_3$–$C_8$-alcohols selected from the group consisting of n-propanol, isopropanol, 1-butanol, 2-butanol, 2-methyl-1-propanol, 2-methyl-2-propanol, 1-pentanol, 1-hexanol and 1-octanol. Very particularly preferred alcohols are n-butanol and n-pentanol.

The alcohol is used in a from 1 to 10 fold, preferably from 2 to 8 fold, particularly preferably from 3 to 6 fold, molar excess, based on the 2-keto-L-gulonic acid or diacetone-2-keto-L-gulonic acid used.

In the course of the esterification reaction, the water not only entrained as solvent but also additionally formed during the esterification can be removed from the reaction space via the gas phase as a lower-boiling azeotrope.

If necessary, after the condensation, phase separation (alcohol/water) can be carried out with recycling of the esterification alcohol. Generally in this case complete dehydration of the recycled alcohol, for example by membrane processes or by distillation, is not necessary, since according to the invention complete dehydration is carried out in the reaction space, for example in the counter-current process.

During the esterification of 2-keto-L-gulonic acid with $C_1$–$C_3$-alcohols, owing to the low boiling points of these alcohols, unwanted losses of alcohols and thus yield losses can occur during the removal of water by distillation. By appropriate supplementation of the alcohol losses during the reaction, the esterification rate may be increased again.

By adding an acid catalyst, the esterification reaction is catalyzed in a manner known per se. The catalyst is used here in amounts of from 0.001 to 0.2 mol, preferably in amounts of from 0.005 to 0.1 mol, particularly preferably from 0.005 to 0.05 mol, per mol of 2-keto-L-gulonic acid or diacetone-2-keto-L-gulonic acid.

Esterification catalysts which can be used are generally all homogeneous or heterogeneous acid catalysts which are known per se.

Preferably, the esterification is carried out in the presence of an acid homogeneous or heterogeneous catalyst selected from the group consisting of mineral acids, organic sulfonic acids, organic carboxylic acids, acidic ion-exchange resins and fixed-bed catalysts having acidic reaction centers, for example acidic zeolites.

Suitable homogeneous catalysts are, for example, mineral acids or their esters. These include, in particular, phosphoric acid, monobutyl phosphate, dibutyl phosphate, monopentyl phosphate, dipentyl phosphate, sulfuric acid, monobutyl sulfate, monopentyl sulfate, hydrogen chloride. Preferred organic sulfonic acids are p-toluenesulfonic acid, methanesulfonic acid, trifluoromethanesulfonic acid and chlorosulfonic acid. Of the organic carboxylic acids, those which may be used as esterification catalysts are trifluoroacetic acid or also 2-keto-L-gulonic acid, diacetone-2-keto-L-gulonic acid or ascorbic acid.

Particular preference is given to using sulfuric acid, p-toluenesulfonic acid, methanesulfonic acid or monoalkylsulfates of the alcohols used. The monoalkylsulfates eliminate sulfuric acid at temperatures above 70° C. [Popelier, Bull. Soc. Chim. Belg. 35 (1926) 265], which then acts catalytically. Very particularly preferred homogeneous acid catalysts are sulfuric acid and p-toluenesulfonic acid.

In the case of the abovementioned homogeneous catalysts, these can either be added to one of the starting materials before the reaction or fed into the reactor as a separate stream.

Heterogeneous catalysts are advantageously fixed in the reactor in the hot reaction zone. Numerous possibilities of construction are described in the literature for installing heterogeneous catalysts in distillation columns. These include residence time trays, in which the catalyst can be arranged on the trays or in their outlet pipes, in addition coated random packings or coated arranged packings, for example ceramic arranged packings, coiled and structured arranged packings having catalyst woven in.

Heterogeneous catalysts which can be used are acid catalysts which are known per se, preferably acid cation exchangers, and also zeolites.

For the purposes of the patent, the "acid cation exchangers" are commercially available resins or Detoxans, for example LEWATIT® S 100, SP 112 or LEWATIT® 2631 (Bayer) or AMBERLITE® 18 and IRA 120 or AMBERLYST® 15 or DUOLITE® C 20, C 26 and C 264 (Rohm & Haas) or DOWEX® ion exchanger.

Zeolites are crystalline aluminosilicates which possess a highly ordered structure having a rigid three-dimensional network of $SiO_4$ or $AlO_4$ tetrahedra, which are linked via shared oxygen atoms. The ratio of Si and Al to oxygen is 1:2. The electrovalency of the aluminum-containing tetrahedra is balanced by including cations in the crystal, for example of an alkali metal or hydrogen. Cation exchange is therefore possible. The spaces between the tetrahedra are occupied by water molecules before the dehydration by drying or calcination.

Suitable zeolites are, for example, those of the Pentasil type, particularly aluminosilicate zeolites or borosilicate zeolites. It is possible, by a partial pre-coke, to set the activity of the catalyst for a selectivity optimum of the desired reaction product.

The esterification is carried out according to the invention at a temperature in the range from 40 to 250° C., preferably from 70 to 200° C., particularly preferably in the range from 80 to 150° C.

The residence time of the reaction mixture in the reaction compartment is in the range from 1 to 2000 seconds, preferably from 20 to 300 seconds, particularly preferably in the range from 30 to 250 seconds.

The esterification is carried out according to the invention in the pressure range from 1 to 2000 mbar and is preferably carried out at from 150 to 1000 mbar, particularly preferably from 200 to 950 mbar.

In addition to 2-keto-L-gulonic acid, diacetone-2-keto-L-gulonic acids can also be esterified in the same manner under the abovementioned conditions. In this case, the acetone protecting group is additionally eliminated. For the elimination, two molar equivalents of water are required, while at the same time one molar equivalent of water is formed in the esterification reactor. In the simplest manner, therefore, the monohydrate of diacetone-2-keto-L-gulonic acid is used. The reaction takes place in the same pressure and temperature ranges as described above. The resultant acetone is distilled off as a low-boiler during the esterification reaction at the beginning or together with excess water-containing solvent, and after isolation and purification, can be recycled and, for example, used to synthesize diacetone-2-keto-L-gulonic acid by the classical Reichstein process. When anhydrous diacetone-2-keto-L-gulonic acid is used, in addition, 1 mol of water must be added.

For the process of the invention, preferably, 2-keto-L-gulonic acid is used as starting material. The acid can be used either in crystalline form, for example as dried or centrifuge-moist monohydrate, as anhydrous compound or as aqueous solution, for example as concentrated fermentation solution.

The monohydrate of 2-keto-L-gulonic acid is generally produced in the crystallization from water or from aqueous organic solvents. Moist monohydrate may be obtained by centrifuging off the crystal mixture. This monohydrate can be used as a centrifuge-moist product directly in the esterification reaction of the invention or can be dried under mild conditions.

Advantageously, in the process of the invention, the drying or dehydration of the monohydrate of 2-keto-L-gulonic acid can be omitted, since in the subsequent activation reaction of the invention an azeotropic dehydration takes place in any case.

The degree of conversion of 2-keto-L-gulonic acid in the esterification reaction is in the process of the invention markedly above 90%, preferably above 95%, particularly preferably in a range from 97 to 99.9%.

The 2-keto-L-gulonic acid $C_1$–$C_{10}$-alkyl ester formed in process step a) is then, in step b) in the presence of an alkali metal $C_1$–$C_{10}$-alkoxide continuously converted into the corresponding alkali metal salt as L-ascorbic acid.

The alcohols used for the alkali metal alkoxides are the $C_1C_{10}$-, preferably $C_3$–$C_{10}$-, particularly preferably $C_3$–$C_8$-alcohols already mentioned at the outset, in particular those compounds selected from the group consisting of n-propanol, isopropanol, 1-butanol, 2-butanol, 2-methyl-1-propanol, 2-methyl-2-propanol, 1-pentanol, 1-hexanol and 1-octanol.

The lactonization in process step b) is carried out according to the invention at a temperature in the range from 40 to 200° C., preferably from 60 to 150° C., particularly preferably in the range from 80 to 120° C.

The residence time of the reaction mixture in the reactor is in the range from 20 seconds to 60 minutes, preferably from 30 seconds to 10 minutes, particularly preferably in the range from 40 seconds to 3 minutes.

The reaction in step b) is carried out according to the invention in the process range from 1 to 4000 mbar and is preferably carried out from 150 to 1000 mbar, particularly preferably from 200 to 950 mbar.

One particular embodiment of the process of the invention is distinguished by the fact that, in an additional process step c), the alkali metal $C_1$–$C_{10}$-alkoxide is generated in situ, for example by reacting the corresponding $C_1$–$C_{10}$-alcohol with an aqueous alkali metal hydroxide solution.

Process step c) is carried out according to the invention at a temperature in the range from 40 to 250° C., preferably from 70 to 200° C., particularly preferably in the range from 80 to 150° C.

The residence time is in the range from 1 to 2000 seconds, preferably from 20 to 300 seconds, particularly preferably in the range from 30 to 250 seconds.

The alkoxide is formed according to the invention in the pressure range from 1 to 4000 mbar and is preferably carried out from 150 to 1000 mbar, particularly preferably from 200 to 950 mbar.

Possible apparatuses for carrying out the continuous process of the invention are, inter alia, falling-film or falling-stream evaporators, Sambay and Luwa thin-film evaporators [=evaporators in which thin liquid films are produced by rotary wiping blades or rollers], rotary evaporators or thin-film rectification columns [for example random packing columns and film columns, rectifiers having rotating internals (spray-towers)]. A more detailed description of the reactors mentioned here may be found in Ullmanns Encyklopadie der technischen Chemie [Ullmanns Encyclopedia of Industrial Chemistry], 4 th edition, Volume 2 (1972), pp. 516, 533–537, 652–660 and in Volume 3 (1973), pp. 386–388.

Preferred reactors are thin-film evaporators or falling-stream evaporators and, particularly preferaby, the reaction columns described, inter alia, in Chem. Ing. Techn. 43 (1971) 1001 reaction columns having stripping and enrichment sections.

The construction of the reaction columns can here be an arrangement of thermally coupled distillation columns or, preferably, what are termed dividing-wall columns.

The reactive distillation preferably used in the process of the invention is disclosed in the literature and, for homogeneously and heterogeneously catalyzed reactions or autocatalytic reactions is described, inter alia, in Chem. Ing. Tech. 50 (1978) 8, 586–592, Chem. Eng. 10 (1998), 158–163 and Chem. Tech., 5 (1997), 37–45 and in EP-A-0 454 719.

In the case of homogeneously catalyzed reactions, generally non-volatile or high-boiling catalysts are used, for example sulfuric acid, p-toluenesulfonic acid, alkali metal hydroxide solutions or alkoxides. However, in individual cases, homogeneous catalysts can also be used, the boiling point of which is in the range of the reactants, for example nitric acid, which, predominantly remain in the column due to the action of distillation.

Heterogeneous catalysts are usually accommodated within the column or in separate containers outside the column in the form of fixed catalyst beds. They can be used as beds, for example in ion-exchange resins, be shaped to form random packings, for example ion exchangers compressed to form Raschig rings, incorporated in filter cloth and shaped to form bales or arranged column packings, applied to arranged distillation packings or used as suspension in the column.

A particular embodiment of the reaction columns is what is termed a dividing-wall column. This type of column is described, for example, in Chem. Eng. Technol. 10 (1987) 92–98, Process Engineering 2 (1993) 33–34 and Chemical Engineering 7 (1997) 72–76.

Thermally coupled distillation columns, which can be implemented in various apparatus designs, are also described in the abovementioned specialist literature references. Dividing-wall columns and thermally coupled columns, compared with the arrangement of conventional distillation columns, offer advantages both with respect to energy consumption and also capital costs and are therefore increasingly being used industrially.

Dividing-wall columns and thermally coupled columns can be designed either as packed columns containing random packings or arranged packings or as tray columns.

EP-A-0 126 288 describes a dividing-wall column in which chemical reactions are carried out. By a defined addition of homogeneous catalysts with respect to the point of addition and their relative volatility to the individual reactants, chemical reactions can be specifically restricted to certain partial regions of the column system. With respect to the use of heterogeneous catalysts, it is stated that they can be used in the form of ion exchangers in residence time containers outside the column body.

The process of the invention is further distinguished by the fact that at least one of the abovementioned process steps a) to c) is carried out in a distillation column, in particular in a dividing-wall column.

Preferably, all three process steps a) to c) are carried out in a shared distillation column.

In this case, in a partial region of the dividing-wall column, the keto-L-gulonic acid or diacetone-2-keto-L-gulonic acid is esterified, in a second partial region the rearrangement to form the ascorbic acid salt is carried out and simultaneously the base required for the rearrangement is prepared in a third partial region.

Very particular preference is given to a process for preparing sodium L-ascorbate wherein in a dividing-wall column, continuously, a) 2-keto-L-gulonic acid is esterified with n-butanol in the presence of sulfuric acid in a separate partial region of the dividing-wall column, simultaneously distilling off the water, b) the resultant 2-keto-L-gulonic acid n-butyl ester is rearranged in the presence of sodium n-butylate to form sodium ascorbate in a further partial region of the dividing-wall column, in which case c) sodium n-butylate is prepared in situ in a third partial region of the dividing-wall column by reacting n-butanol with an aqueous sodium hydroxide solution, simultaneously distilling off the water.

The esterification with n-butanol in process step a) is performed in a temperature range from 80 to 150° C., in a pressure range from 200 to 950 mbar and at a residence time of from 30 to 250 seconds.

The rearrangement to give sodium L-ascorbate in process step b) is performed in a temperature range from 80 to 120° C., in a pressure range from 200 to 950 mbar and at a residence time of from 40 seconds to 3 minutes.

Sodium n-butylate is prepared in process step c) in a temperature range from 80 to 150° C., in a pressure range from 200 to 950 mbar and at a residence time of from 30 to 250 seconds.

On the basis of FIG. 1, the apparatus preferred for the process of the invention—the dividing-wall column—will be described in more detail for the example of sodium L-ascorbate from 2-keto-L-gulonic acid.

In the dividing-wall column, the aqueous or alcoholic solution of 2-keto-L-gulonic acid (KGA) is firstly further concentrated in partial region 4 and esterified in the same partial region 4 by reaction with the alcohol, preferably butanol, in the presence of the catalyst acid, preferably sulfuric acid or an acidic supported catalyst. The ester leaves the partial region 4 as alcoholic solution.

To produce the keto-L-gulonic ester in the reaction column, preferably an aqueous solution of the free acid is used in a concentration range from 10 to 60% by weight.

In another segment of the divided column, in partial region 5, anhydrous alkali metal alkoxide, preferably sodium butoxide, is prepared by feeding aqueous sodium hydroxide solution and reacting it with the simultaneously added butanol. The alkali metal alkoxide formed at the end of partial region 5 is transferred into bed 6. There, the further rearrangement of the ester to form the alkali metal ascorbate, in particular sodium L-ascorbate takes place. The reaction conditions and dimensions of the partial region 6 are adjusted in this case so that the resultant alkali metal ascorbate does not precipitate out until in the lower part of the packing and leaves the column as a suspension.

The remaining dehydration of the overhead products from the esterification and alkoxide formation is carried out in partial region 1 of the dividing-wall column. When butanol is used, the azeotrope water/n-butanol is removed at the top of the column and passed through a phase separator. The moist n-butanol is recirculated to the column top. In addition, fresh butanol can be fed in at this position.

Instead of water, other polar solvents are also useful, preferably alcohols or solvent mixtures, in order to prepare a solution of 2-keto-L-gulonic acid for the reactive distillation.

Numerous possible constructions are described in the literature for the installation of heterogeneous catalysts in distillation columns. These include residence time trays, in which the catalyst can be arranged on the trays or in their outlet pipes, in addition coated random packings, coiled and structured arranged packings having catalyst woven in. For these, any acid catalysts, for example ion exchangers, zeolites or inert supports doped with acidic centers, can also be used.

The position of addition of the liquid homogeneous acid catalysts into the reaction column depends on the operating parameters. The position varies from simultaneous addition with the alcohol at the top of the column to a separate metering position in the stripping section. The type of addition varies with the reaction temperature, the operating pressure and the temperature stability of the catalysts. A higher reaction rate permits a more compact form of the apparatus.

The temperature ranges mentioned at the outset must be selected so that the catalyst, the starting materials and the reaction product are not damaged. At the same time, it is desirable to keep the condensation temperatures significantly above the ambient temperature.

To prepare the alkali metal alkoxide, the same temperature and pressure ranges are employed as are used to prepare the ester. In the case of the butoxide, atmospheric pressure or a slightly reduced pressure is employed in the temperature range from 100 to 130° C.

It is also possible to carry out process step b) in a reactor separated from the distillation column.

A process of this type, which is also preferred, is distinguished in the fact that in a dividing-wall column, continuously, a) 2-keto-L-gulonic acid is esterified with n-butanol in the presence of sulfuric acid in a separate partial region of the dividing-wall column, simultaneously distilling off the water, b) the resultant 2-keto-L-gulonic acid n-butyl ester is continuously rearranged in the presence of sodium n-butylate to form sodium ascorbate in a reaction mixing pump separate from the dividing-wall column, in which case c) sodium n-butylate is prepared in situ in a further separate partial region of the dividing-wall column specified under a) by reacting n-butanol with an aqueous sodium hydroxide solution, simultaneously distilling off the water.

The pressure, temperature and residence time parameters of the individual steps a) to c) are here also in the ranges already mentioned above.

Figure 2:
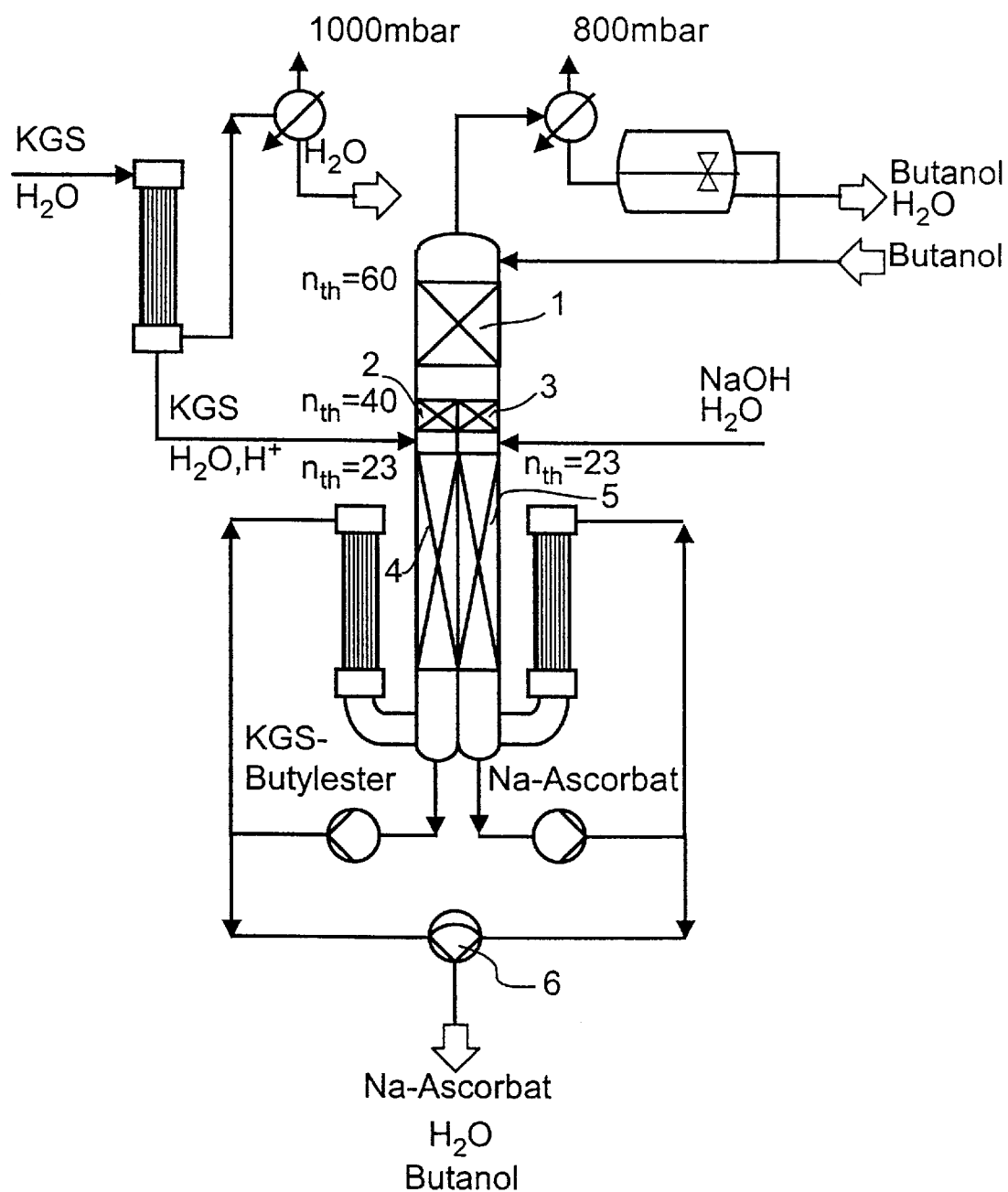

Thus, in accordance with FIG. 2, the product streams of the 2-keto-L-gulonic ester and the alkali metal alkoxide can be taken off separately from the dividing-wall column, then combined in a reaction mixing pump (6) and converted into alkali metal ascorbate and the suspension which may be formed can be fed to a downstream workup stage. Alternatively to the reaction mixing pump, cylinder rolls or jet nozzle reactors can also be used for the lactonization step.

Likewise, the alkali metal $C_1$–$C_{10}$-alkoxide can also be prepared in separate reactors in order then to catalyze the rearrangement of the 2-keto-L-gulonic ester continuously by feeding it into one of the abovedescribed reactors.

The continuous process of the invention for preparing alkali metal salts of L-ascorbic acid is distinguished by a number of advantages:

The overall residence times are very short, compared with the literature-known embodiments of ascorbate syntheses starting from 2-keto-L-gulonic acid.

As a result, apparatuses of smaller dimensions can be used.

The equilibrium conversions in the esterification are high, as a result of which the reaction product in each case according to specific intensive reaction parameters, has a residual content of only from 0.02 to 0.5% by weight of unreacted 2-keto-L-gulonic acid.

The operating conditions during the stripping distillation can be set so that the water content and if appropriate also the esterification alcohol content in the reaction mixture approach zero.

The continuous preparation of alkoxide can be performed in the same distillation column with complete dehydration.

In the column water is eliminated and butanol is recovered.

The residual dehydration of the keto-L-gulonic acid solution is also performed in the same apparatus.

The process of the invention will be described in more detail with reference to the example below.

EXAMPLE 1

Preparation of Sodium L-ascorbate

The continuous preparation of 2-keto-L-gulonic acid n-butyl ester and sodium n-butoxide and subsequent rearrangement to form sodium L-ascorbate were carried out in a dividing-wall column according to FIG. 1.

The experimental column had a diameter of 0.2 m. The column was fitted over a height of 20 m with sheet metal packings having a specific surface area of 350 m$^2$/m$^3$. The number of theoretical plates of the column was in total 60 plates. The dividing wall of the column was mounted by welding between the 15$_{th}$ and 40$_{th}$ stage (counted from the bottom). The liquid was divided between the partial regions 2 and 3 of the column in a ratio of 2:1. The column was operated at a top pressure of 800 mbar. The feed to the esterification side of the dividing-wall column (partial regions 2 and 4) was 62.5 kg/h in the form of a 50% strength by weight aqueous 2-keto-L-gulonic acid solution. The sulfuric acid used as catalyst was added as a 5% strength by weight butanolic solution at a rate of 7.25 kg/h.

128 kg/h of 50% sodium hydroxide solution were run in on the alkoxide side of the dividing-wall column (partial regions 3 and 5).

The n-butanol/water azeotrope produced in the enrichment part 1 was condensed at the top of the column and fed to a phase separation vessel. The butanol phase was recirculated to the top of the column. The aqueous phase was introduced into the stripping part of the column at the tenth theoretical plate (counted from the bottom).

In a suitable packing 6, the ester and alkoxide product streams were combined and rapidly removed from the column. The slightly yellowish suspension contained sodium L-ascorbate. After filtration, washing with n-butanol and drying under reduced pressure, crude sodium L-ascorbate having a purity of 98% was isolated in a yield of 94%.

We claim:

1. A process for preparing alkali metal salts of L-ascorbic acid comprising the following steps:
   a) esterifying 2-keto-L-gulonic acid or diacetone-2-keto-L-gulonic acid with a $C_1$–$C_{10}$-alkohol in the presence of an acid catalyst,
   b) rearranging the 2-keto-L-gulonic acid $C_1$–$C_{10}$-alkyl ester formed in the presence of an alkali metal $C_1$–$C_{10}$-alkoxide,
   which comprises carrying out each of the process steps a) and b) continuously.

2. A process as claimed in claim 1 wherein, in process step a), the esterification is carried out using a $C_3$–$C_8$-alcohol, selected from the group consisting of n-propanol, isopropanol, 1-butanol, 2-butanol, 2-methyl-1-propanol, 2-methyl-2-propanol, 1-pentanol, 1-hexanol and 1-octanol.

3. A process as claimed in claim 1 wherein the esterification is carried out in the presence of an acid catalyst selected from the group consisting of mineral acids, organic sulfonic acids, organic carboxylic acids, acidic ion-exchange resins and fixed-bed catalysts having acidic reaction centers.

4. A process as claimed in claim 1 wherein, in process step b), the rearrangement is carried out in the presence of an alkali metal alkoxide of a $C_3$–$C_8$-alcohol selected from the group consisting of n-propanol, isopropanol, 1-butanol, 2-butanol, 2-methyl-1-propanol, 2-methyl-2-propanol, 1-pentanol, 1-hexanol and 1-octanol.

5. A process as claimed in claim 1 wherein, in an additional process step c), the alkali metal $C_1$–$C_{10}$-alkoxide is generated in situ.

6. The process as claimed in claim 5 wherein the alkali metal alkoxide is prepared in process step c) in a temperature range from 40 to 250° C., in a pressure range from 1 to 4000 mbar and at a residence time of from 1 to 2000 seconds.

7. A process as claimed in claim 1 wherein the esterification in process step a) is carried out in a temperature range from 40 to 250° C., in a pressure range from 1 to 2000 mbar and at a residence time of from 1 to 2000 seconds.

8. A process as claimed in claim 1 wherein the rearrangement in process step b) is carried out in a temperature range from 40 to 200° C., in a pressure range from 1 to 4000 mbar and at a residence time of from 20 seconds to 60 minutes.

9. A process as claimed in claim 5 wherein at least one of the process steps a) to c) is carried out in a distillation column.

10. A process as claimed in claim 9 wherein the distillation column is a dividing-wall column.

11. A process as claimed in claim 9 wherein all three process steps a) to c) are carried out in a shared distillation column.

12. A process as claimed in claim 9 wherein process step b) is carried out in a reactor separate from the distillation column.

13. A process as claimed in claim 11 wherein, in a dividing-wall column, continuously,
   a) 2-keto-L-gulonic acid is esterified with n-butanol in the presence of sulfuric acid in a separate partial region of the dividing-wall column, simultaneously distilling off the water,
   b) the resultant 2-keto-L-gulonic acid n-butyl ester is rearranged in the presence of sodium n-butylate to form sodium ascorbate in a further partial region of the dividing-wall column, in which case
   c) sodium n-butylate is prepared in situ in a third partial region of the dividing-wall column by reacting n-butanol with an aqueous sodium hydroxide solution, simultaneously distilling off the water.

14. A process as claimed in claim 12 wherein, in a dividing-wall column, continuously,
   a) 2-keto-L-gulonic acid is esterified with n-butanol in the presence of sulfuric acid in a separate partial region of the dividing-wall column, simultaneously distilling off the water,
   b) the resultant 2-keto-L-gulonic acid n-butyl ester is continuously rearranged in the presence of sodium n-butylate to form sodium ascorbate in a reaction mixing pump separate from the dividing-wall column, in which case
   c) sodium n-butylate is prepared in situ in a further separate partial region of the dividing-wall column specified under a) by reacting n-butanol with an aqueous sodium hydroxide solution, simultaneously distilling off the water.

15. A process as claimed in claim 13 wherein the esterification in process step a) is carried out in a temperature range from 80 to 150° C., in a pressure range from 200 to 950 mbar and at a residence time of from 30 to 250 seconds.

16. A process as claimed in claim 13 wherein the rearrangement in process step b) is carried out in a temperature range from 80 to 120° C., in a pressure range from 200 to 950 mbar and at a residence time of from 40 seconds to 3 minutes.

17. A process as claimed in claim 13 wherein the sodium n-butylate is prepared in process step c) in a temperature range from 80 to 150° C., in a pressure range from 200 to 950 mbar and at a residence time of from 30 to 250 seconds.

* * * * *